United States Patent [19]

McClure

[11] 4,023,417
[45] May 17, 1977

[54] LIQUID SAMPLING

[75] Inventor: Charles Laird McClure, Malvern, Pa.

[73] Assignee: Pro-Tech Inc., Paoli, Pa.

[22] Filed: Feb. 3, 1975

[21] Appl. No.: 546,632

Related U.S. Application Data

[63] Continuation of Ser. No. 369,722, June 13, 1973, Pat. No. 3,863,506.

[52] U.S. Cl. .............................................. 73/421 B
[51] Int. Cl.$^2$ ....................................... G01N 1/14
[58] Field of Search ............ 73/421 R, 421 B, 422, 73/423 A; 307/141, 141.8; 417/145, 146, 147; 137/113

[56] References Cited

UNITED STATES PATENTS

| | | | |
|---|---|---|---|
| 2,408,799 | 10/1946 | Melchar | 137/113 |
| 2,885,001 | 5/1959 | Brown | 200/35 R |
| 3,120,128 | 2/1964 | Snyder | 73/421 B |
| 3,335,298 | 8/1967 | Craig | 307/141 |
| 3,604,269 | 9/1971 | Smith et al. | 73/423 A |
| 3,719,081 | 3/1973 | Lynn et al. | 73/421 B |
| 3,720,109 | 3/1973 | Blechman | 73/421 B |
| 3,727,464 | 4/1973 | Rutkowski et al. | 73/421 B |
| 3,750,477 | 8/1973 | Rutkowski et al. | 73/421 B |
| 3,811,324 | 5/1974 | Doncer et al. | 73/421 B |

FOREIGN PATENTS OR APPLICATIONS 649,081  8/1928  France ............................. 417/145

*Primary Examiner*—S. Clement Swisher
*Attorney, Agent, or Firm*—Charles A. McClure

[57] ABSTRACT

Electrically actuated apparatus for sampling liquid from a body thereof provides visible countdown of the time interval between successive samplings and also provides visible countdown of the duration of the time in which individual samples are being taken. The samples are propelled by fluid from an external or internal source of pressure, whichever is greater, interconnected for each sample duration period to a sample intake chamber in the body of liquid being sampled.

11 Claims, 5 Drawing Figures

LIQUID SAMPLING

This is a continuation, of application Serial No. 369,722, filed June 13, 1973 now U.S. Pat. No. 3,863,506.

This invention relates to sampling of a liquid medium, as for determination of the composition thereof or of contaminants therein, and concerns especially electrically actuated apparatus for doing so by utilizing a pressurized fluid to propel the liquid samples.

As automatic sampling means and methods for sampling liquid have developed, a division into two main classes has occurred: pressure-actuated and electrically actuated. The functions performed by the selected power source, whether fluid pressure or electricity, include timing the interval between successive samples, timing the duration of individual samples, and valve switching between a condition of interconnection to the liquid medium to propel a sample therefrom and an alternative condition of disconnection from the liquid medium until it is time to take the next sample. Each has its disadvantages, as well as its advantages, of course.

A primary object of the present invention is electrical timing and valve switching but fluid propulsion of liquid samples.

Another object is instantaneous change-over between internal and external sources of pressurized propellant fluid.

A further object is interchangeability between use of automatic operation at the instance of electrical timing signals generated internally and, alternatively, external electrical signals, which may be proportional to flow of the liquid being sampled.

Yet another object is visible countdown of both sampling interval (i.e., the time period between successive samples) and sample duration (i.e., the time period during which propellant fluid is being piped to the sampling locus in the liquid being sampled).

Other objects of this invention, together with means and methods for attaining the various objects, will be apparent from the following description and the accompanying diagrams of a preferred apparatus embodiment, which is presented by way of example rather than limitation.

In general, the objects of the present invention are accomplished, in apparatus for sampling liquid from a body thereof at predetermined intervals of time and for predetermined periods of time at each sampling, by electrical means for determining the sampling interval, electrical means for determining the duration of sampling, conduit means to and from the body of liquid and adapted to receive gaseous fluid at superatmospheric pressure to propel samples of liquid from the body thereof to a collection location during sampling periods.

Figure 1:
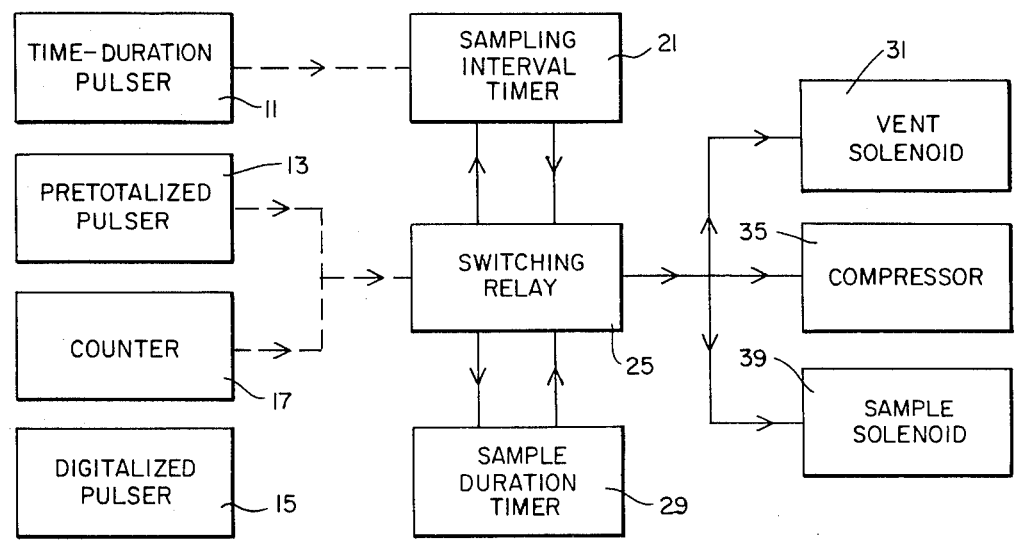
FIG. 1 is a block diagram of electrical apparatus according to the present invention.

FIG. 1 shows in block form Switching Relay 25 interposed between Sampling Interval Timer 21 and Sample Duration Timer 29, with oppositely directed pairs of arrows linking the relay with each of the timers. Interconnected in parallel to the relay, as indicated by arrows leading therefrom, are Vent Solenoid 31, Compressor 35, and Sample Solenoid 39. Interconnectable to the sampling interval timer, as indicated by broken lines with arrow leading thereto, is Time-Duration Pulser 11. Similarly connectable to the sample duration timer through the switching relay are Pretotalized Pulser 13 and (alternatively) Counter 17 fed by Digitalized Pulser 15. Further details appear in a subsequent schematic circuit diagram.

Figure 2:
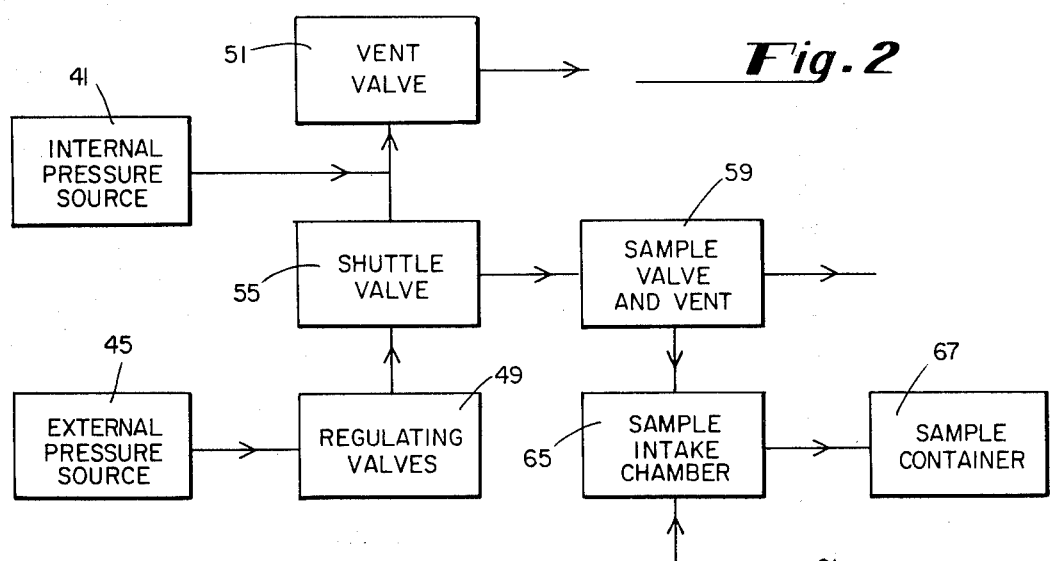
FIG. 2 is a block diagram of pneumatic and hydraulic apparatus according to the invention.

FIG. 2 shows in block form Shuttle Valve 55 interposed between Internal Pressure Source 41 and External Pressure Source 45, as indicated by arrows leading from each of the latter two components to the former. Vent Valve 51 parallels the shuttle valve downstream from the internal source, while the line from the external source contains regulating valves 49. Interposed in series downstream of the shuttle valve are Sample Valve and Vent 59, Sample Intake Chamber 65, and Sample Container 67. Upstream of the chamber are Liquid to be Sampled 61 and intervening Check Valve 63. Further details appear in the next view.

Figure 3:
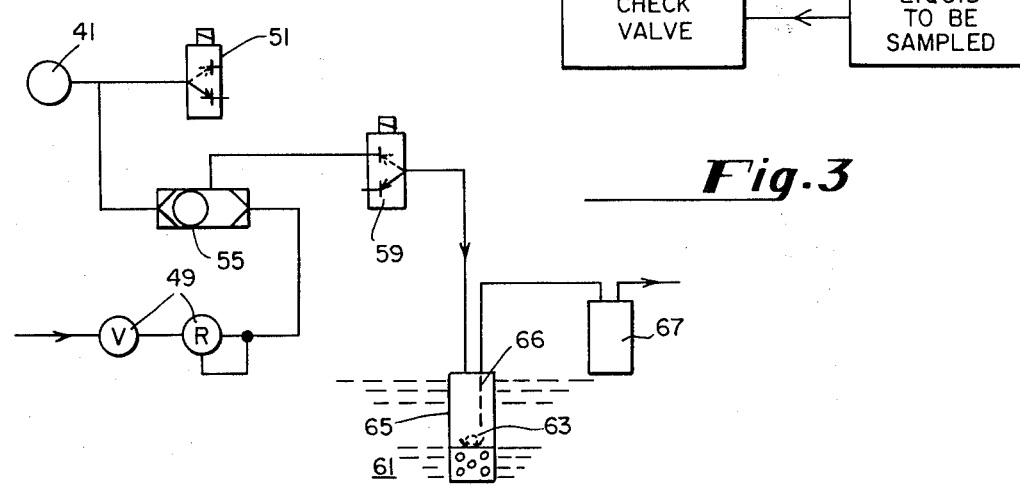
FIG. 3 is a schematic circuit diagram of the apparatus of FIG. 2.

FIG. 3 shows fluid circuitry of this invention, corresponding to the block diagram in the last view, Vent Valve 51 is normally in the venting position. Shuttle Valve 55 is in whichever position corresponds to connection of the higher pressure source (internal 41 or external through valve V and regulator R (collectively identified as 49) to sample valve (and vent) 59, which normally is in the position of venting sample chamber 65 and thus does not pass pressurized propellant to the chamber until switched. In the normally venting position of the sample valve, liquid from body 61 thereof can enter the sample chamber through check valve 63 (shown in broken lines). In the switched position of the sample valve, the check valve seals under the pressure of incoming propellant from whichever source, whereupon the liquid contents are forced out dip tube 66 (also shown in broken lines) through the interconnecting tubing to sample container 67, which is vented to the atmosphere.

Figure 4:
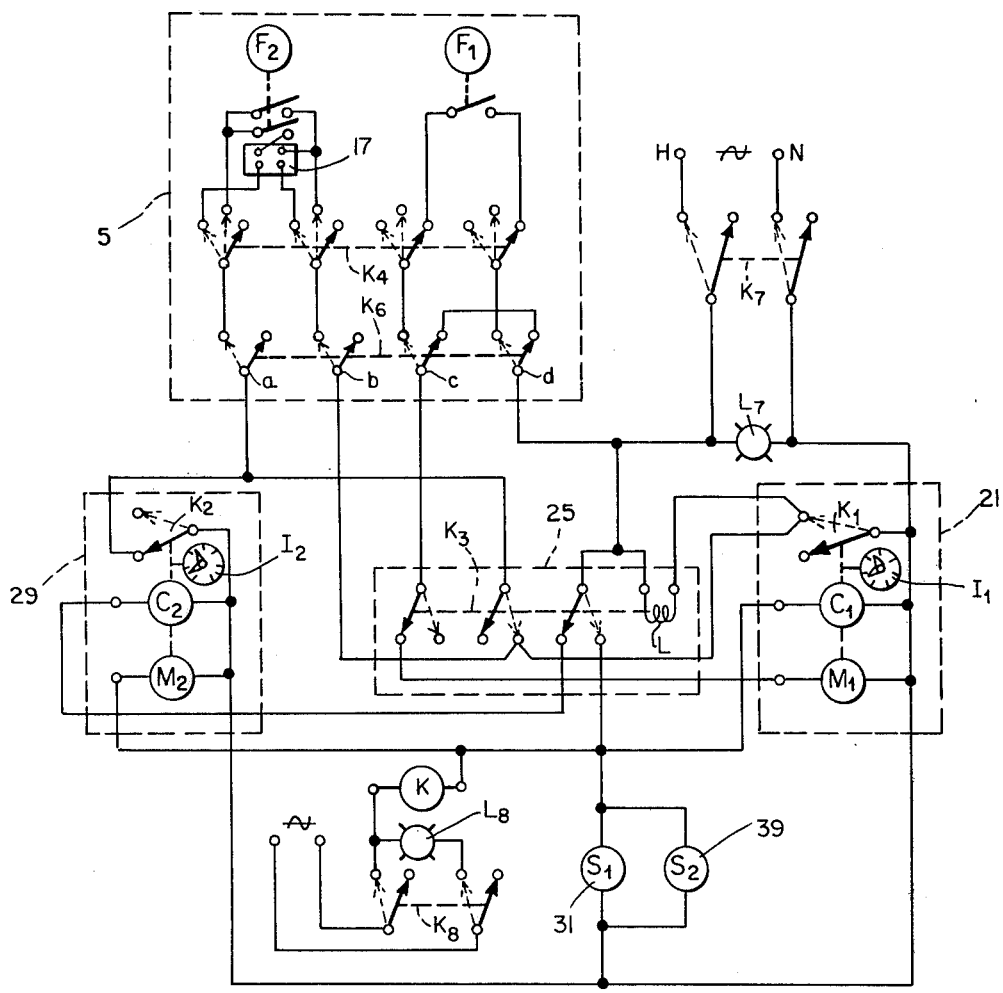
FIG. 4 is a schematic circuit diagram for the electrical apparatus of FIG. 1.

FIG. 4 shows schematically electrical circuitry corresponding to the block diagram of FIG. 1. Respective sampling interval and sample duration timers 21 and 29 are outlined in broken lines at the right and left. Each timer comprises a motor, a clutch, a countdown indicator, and a switch interconnected mechanically, as indicated by broken lines, such that activation of the motor moves the countdown indicator continuously toward its zero position and eventually moves the switch arm from the normal position (shown in solid) to the alternative position (shown in broken lines). The timer construction is such that upon inactivation of the motor (and concurrent declutching) the switch arm is spring-biased back to its original position, together with the countdown indicator. Switching relay 25 is outlined in broken lines and comprises actuating coil L and triple-pole double-throw switch $K_3$ shown normally positioned to the left and with an alternative actuated position to the right.

Outlined in broken lines at the upper left in FIG. 4 is flow-proportional (FP) adapting component, which corresponds generally to the left bank of blocks in FIG. 1. Flowmeter $F_1$, with its switch shown interconnected thereto by broken lines, corresponds to time-duration pulser 11. Flowmeter $F_2$ with its similar switch is adapted to function through its upper switch arm as pretotalized pulser 13, and through its lower switch arm as digitalized pulser 15 by reason of counter 17 having its input terminals connected in series therewith. Quadruple-pole triple-throw FP mode switch $K_4$ is interposed between the flowmeter switches and the counter, on the one hand, and quadruple-pole double-throw AUTOMATIC-FLOW PROPORTIONAL (AUTO-FP) switch $K_6$ on the other hand, all within FP adapter component 5.

For ready reference the four leads from that FP component are identified by reference to $K_6$ switch arm contact or pivot points, from left to right, as $a$, $b$, $c$, $d$. The lead from contact $a$ connects to the normally closed contact of sample duration timer switch $K_2$ and to the middle of switch $K_3$ and switching relay 25. The lead from contact $b$ interconnects to the normally open contact of the same arm of switch $K_3$ and to the normally open contact of sampling interval timer switch $K_1$. The lead from contact $c$ connects to one side of main power switch $K_7$, through which it is connectable to high side H of the supply power line. The neutral or N side of the power line is connectable through the other side of that switch to the switch arm of sampling interval timer switch $K_1$, as well as to one side of motor $M_1$ and clutch $C_1$ thereof and of motor $M_2$ and clutch $C_2$ of the sample duration timer, also vent solenoid $S_1$ and sample solenoid $S_2$. The H power lead reaches the opposite side of the solenoids and of clutch $C_1$ and motor $M_2$, also one side of compressor K via the normally open contact of the right arm of the switchng relay, whose coil is connected between that lead and the normally open contact of switch $K_1$. The other side of the compressor is connectable to the N power lead via one side of switch $K_8$. Pilot lamps $L_7$ and $L_8$ across respective power switches $K_7$ and $K_8$ indicate their ON position.

Operation of the apparatus of this invention, which is readily understood by reference to the foregoing description and the diagrams, will be described first by reference to the action with switch $K_6$ in its right or AUTOMATIC (AUTO) position, which excludes any further consideration of the FP adapter component.

Sampling interval timer motor $M_1$ is supplied with power through the N lead from one side of switch $K_7$ (which is closed to apply main power) and through the H lead from the other side of that switch, through the jumper across the two rightmost normally closed contacts of AUTO-FP switch $K_6$, through the normally closed leftmost contact of switching relay switch $K_3$. After a time interval determined by internal setting of conventional gear reductions (not shown) to a predetermined time-equivalent value, $M_1$ closes its normally open switch $K_1$ through normally connected clutch $C_1$, whereupon electric power is supplied across coil L of switching relay 25 and the three arms of switch $K_3$ are thrown from their normal left positions to their actuated right positions. Throwing of the left arm removes the power from motor $M_1$, which stops; throwing of the middle arm applies power to the FP adapter component (which will be discussed separately); and throwing of the right arm of switch $K_3$ removes power from sample duration timer clutch $C_2$, which was being held declutched thereby, and applies it to motor $M_2$ of that timer (which begins to run) and to sampling duration timer clutch $C_1$, which is declutched thereby—permitting switch $K_1$ to be released to its normally open position. Notwithstanding the opening of switch $K_1$, the switching relay is retained in its actuated position by alternative N lead path closed thereby through the middle arm of relay switch $K_3$ and the normally closed arm of sample duration timer switch $K_2$.

Application of power to solenoid $S_1$ when switching relay 25 is actuated closes normally open vent valve 51 (FIG. 3), as well as actuating compressor K of internal pressure source 41 (if switch $K_8$ is thrown) to supply air under superatmospheric pressure to shuttle valve 55. Simultaneous actuation of solenoid $S_2$ closes sample valve vent and interconnects whichever pressure source has the higher pressure, from the shuttle valve, to the interior of sample chamber 65, thereby closing intake check valve 63 and forcing the liquid contents of the chamber through dip tube 66 and the interconnecting tubing into sample container 67, any excess air or externally supplied propellant being vented therefrom.

When sample duration timer motor $M_2$ has run for the desired period (predetermined similarly to that for $M_1$) it opens switch $K_2$, thereby interrupting power to the switching relay, which returns to its original position, removing power from motor $M_2$ and from compressor K and solenoids $S_1$ and $S_2$ but applying power (through the right arm of switch $K_3$) to clutch $C_2$, de-switching it and permitting the arm of switch $K_2$ to return to its normally closed position. Sampling interval timer 21 is reactivated by the release of the switching relay, and the timer recycles. Thus in the AUTO mode, the respective timers (21 and 29) operate alternately so long as the apparatus has power applied thereto, whether the power switch for compressor K is thrown or not, as is optional when an external pressure source is being used.

Operation of FP adapter component 5 is readily understood as a variant of the operation just described. With switch $K_6$ thrown to the left or FP position, flowmeters $F_1$ and $F_2$ are interconnectable to the body of the apparatus through setting of FP MODE switch $K_4$. The mode switch is shown in the rightmost or TIME DURATION (TD) position, in which the switch of flowmeter F is connected in circuit between power lead H from main power switch $K_7$ through the AUTO-FP switch to sampling interval timer motor $M_1$ through normally closed leftmost contact of switch $K_3$. Accordingly, closing of the $F_1$ switch actuates motor $M_1$, which runs so long as the switch is closed, thereby totalizing successive closure periods of that flowmeter switch up until an entire sampling interval is completed, whereupon the switching relay is actuated as before to effect sample recovery.

In the other positions of the FP MODE switch flowmeter $F_2$ is interconnected either directly through the middle position thereof, or indirectly through digital pulse counter 17 in the leftmost position. In the midposition, whenever flowmeter $F_2$ closes its upper switch, a so-called "pretotalized" pulse is applied through a power circuit completed to coil L of switching relay 25 through normally closed switch $K_2$ of the sample duration timer, thereby actuating the relay independently of the sampling interval timer and effecting a cycle of sample recovery. In the left position of the FP MODE switch, flowmeter $F_2$ supplies a digital pulse every time its lower switch closes to connect counter 17 in a series with the power source in like manner, and when the counter has tallied a preset number of such pulses it closes the power circuit to coil L and effects sample recovery as already described. It will be understood that the switching action of the respective flowmeters is an indication of the flow of a given volume of liquid past the sample chamber in the body to be sampled, so that sampling is proportioned to such volume, thereby rendering a composite of a succession of samples more nearly representative of the liquid that has flowed by than if sampling has proceeded automatically at regular intervals.

Figure 5:
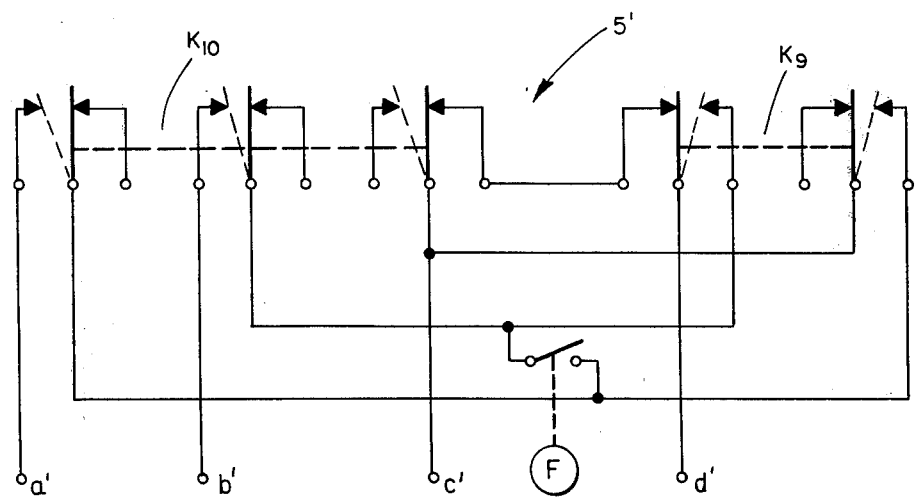
FIG. 5 is a schematic diagram of alternative circuitry for part of FIGS. 1 and 4.

FIG. 5 shows a simplified alternative construction of FP adapter component, designated as 5', in which flowmeter F may deliver either pretotalized or time-duration pulses (i.e., contact closures) with the same effect as just described. A three-position switch is shown in its central or AUTOMATIC position. The four leads at the bottom of the view have contacts designated $a'$, $b'$, $c'$, and $d'$, which correspond to and can be substituted for respective contacts $a$, $b$, $c$, and $d$ of component 5 in FIG. 4. Double-pole switch component $K_9$ at the right, when thrown to the right, puts the apparatus in a TD FP mode of operation (as in the rightmost position of switch $K_4$ in component 5), whereas triple-pole switch component $K_{10}$ at the left, when thrown to the left, puts the apparatus in PT FP mode (as in the midposition of switch $K_4$). It will be understood that movement of respective switch components $K_9$ and $K_{10}$ of this three-position switch do not affect one another. A prime advantage of this alternative arrangement is that only a single pair of contacts is required to accommodate FP signals of either TD or PT type. This modification can be adapted to use with a digitalized pulse flowmeter by incorporating the counter in the flowmeter circuit.

Both sampling interval and sample duration timers are conveniently furnished with conventional dial and moving pointer indicators ($I_1$ and $I_2$) for visual countdown of the timer period remaining in the sampling interval or sample duration period, as the case may be. Pilot lights (not shown) parallelling the respective motors also facilitate observation of the timer actuated at any given moment. The timers, which have similar synchronous motors, may have similar or different gear reductions for the same or different timing ranges. In normal practice, it is convenient to have a range from a minute or so to about a day or so for the sampling interval timer, depending upon desired sampling frequency; and a range from a few seconds to about a minute for the sample duration timer, depending upon sample head or lift and upon length and diameter of sample lines. Such timers are readily available commercially, as are all the other parts of the described apparatus.

This apparatus and the methods of automatic and flow-proportional sampling disclosed here represent a highly versatile and effective advance in the art of liquid sampling, whose convenience and effectiveness will be best appreciated and understood by those undertaking to practice it. Although a principal embodiment and at least one modification have been described and illustrated, the invention is not to be deemed limited thereto. Additional modifications may be made therein, as by addition, combination, or subdivision or parts and steps, while retaining advantages and benefits of the invention, which itself is defined in the following claims.

I claim:

1. In pneumatically sampling liquid from a body thereof at predetermined intervals of time and for predetermined periods of time at each sampling, the combination of determining the sampling interval, determining the duration of sample propulsion, and displaying the time remaining in any current sampling interval and in any current period of sample propulsion.

2. Liquid sampling according to claim 1, including providing a constant sampling interval by repetitive internal timing at constant rate.

3. Liquid sampling according to claim 1, including providing a variable sampling interval by repetitive external timing proportional to flow of liquid in the body being sampled.

4. Liquid sampling according to claim 1, including providing a constant sampling interval by repetitive internal timing at constant rate and, alternatively, a variable sampling interval by repetitive external timing proportional to flow of liquid in the body being sampled, and providing for instantaneously switching from one timing method to the other.

5. In pneumatically sampling liquid from a body thereof at predetermined intervals of time and for predetermined periods of time at each sampling, the combination of determining the sampling interval, determining the duration of sampling, wherein the duration of sampling comprises time for sample propulsion from the body of liquid to the collection location and time for purging the sample propulsion path of liquid, and displaying the time remaining in any current sampling interval and in any current sampling period.

6. In pneumatically sampling liquid from a body thereof at predetermined intervals of time and for predetermined periods of time at each sampling, the combination of determining the sampling interval, determining the duration of sample propulsion, predetermining the sample volume collected during each propulsion period independnently of the duration of such propulsion periods, and displaying the time remaining in any current sampling interval and in any current period of sample propulsion.

7. Liquid sampling according to claim 1, including providing alternative sources of propulsion fluid and interconnecting them in shuttle manner, whereupon the source having the higher pressure closes off the other source and propels the samples during periods of sample propulsion.

8. In sampling liquid from a body thereof at predetermined intervals of time and for predetermined periods of time at each sampling, the steps of adjustably predetermining the sampling interval, adjustably predetermining the duration of sampling, and conducting gaseous fluid at superatmospheric pressure to a body of liquid to be sampled so as to propel samples of liquid therefrom to a collection location during the sampling periods, including providing an internal source of gaseous fluid at superatmospheric pressure and providing an inlet for gaseous fluid at superatmospheric pressure from an external source thereof, and, during the sampling periods only, interconnecting the external inlet to the body of liquid when the external gaseous fluid pressure exceeds a given value and otherwise connecting the internal pressure source thereto to propel samples of liquid therefrom.

9. Liquid sampling according to claim 4, wherein the internal source comprises compressed air.

10. Liquid sampling according to claim 1, including alternately permitting and precluding such flow of propellant during the sampling periods and sample propulsion intervals, respectively.

11. Liquid sampling according to claim 2, wherein the sample propulsion interval and sampling duration are determined by preselecting an appropriate period of time for each independently of one another.

* * * * *